(12) United States Patent
Miller et al.

(10) Patent No.: US 6,232,060 B1
(45) Date of Patent: *May 15, 2001

(54) ASSAY SYSTEM FOR ANTI-STRESS AGENTS

(75) Inventors: Guy Miller, Mountain View; Margaret A. Hirst, Redwood City, both of CA (US)

(73) Assignee: Galileo Laboratories, Inc., Santa Clara, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/588,893

(22) Filed: Jan. 19, 1996

(51) Int. Cl.$^7$ ............... C12Q 1/00; C12Q 1/26; G01N 33/566
(52) U.S. Cl. ............... 435/4; 435/25; 435/26; 435/190; 436/501; 436/164
(58) Field of Search ............... 436/503, 501, 436/164, 35, 50; 530/300, 350; 435/4, 25, 190, 426

(56) References Cited

U.S. PATENT DOCUMENTS 5,198,336 * 3/1993 Knobeloch et al. ............... 435/4

OTHER PUBLICATIONS

Marsh et al., Hepatology., 17(1), pp. 91–98, 1993.*

Jackson M J et al., Clinical Science, 80(6), pp. 559–564, Jun. 1991.*

Ihrke et al., "WIF–B Cells: An In Vitro Model for Studies of Hepatocyte Polarity," The J. of Cell Biology (1993), 123:1762–1775.

Shanks et al., "An Improved Polarized Rat Hepatoma Hybrid Cell Line," J. of Cell Science (1994), 107:813–825.

* cited by examiner

*Primary Examiner*—Jyothsna Venkat
*Assistant Examiner*—P. Ponnaluri
(74) *Attorney, Agent, or Firm*—Morrison & Foerster, LLP

(57) ABSTRACT

Methods and compositions are provided for screening compounds for anti-stress activity. A rat hepatoma-derived cell line is employed, which is particularly responsive to mitochondrial function inhibiting agents, demonstrated by the extracellular release of lactate dehydrogenase and the formation of lactate. Cytoprotectant agents are shown to reverse the lactate dehydrogenase release in the presence of mitochondrial function interfering agents, as a model for the effects of hypoxia on cellular energetic function.

10 Claims, 3 Drawing Sheets

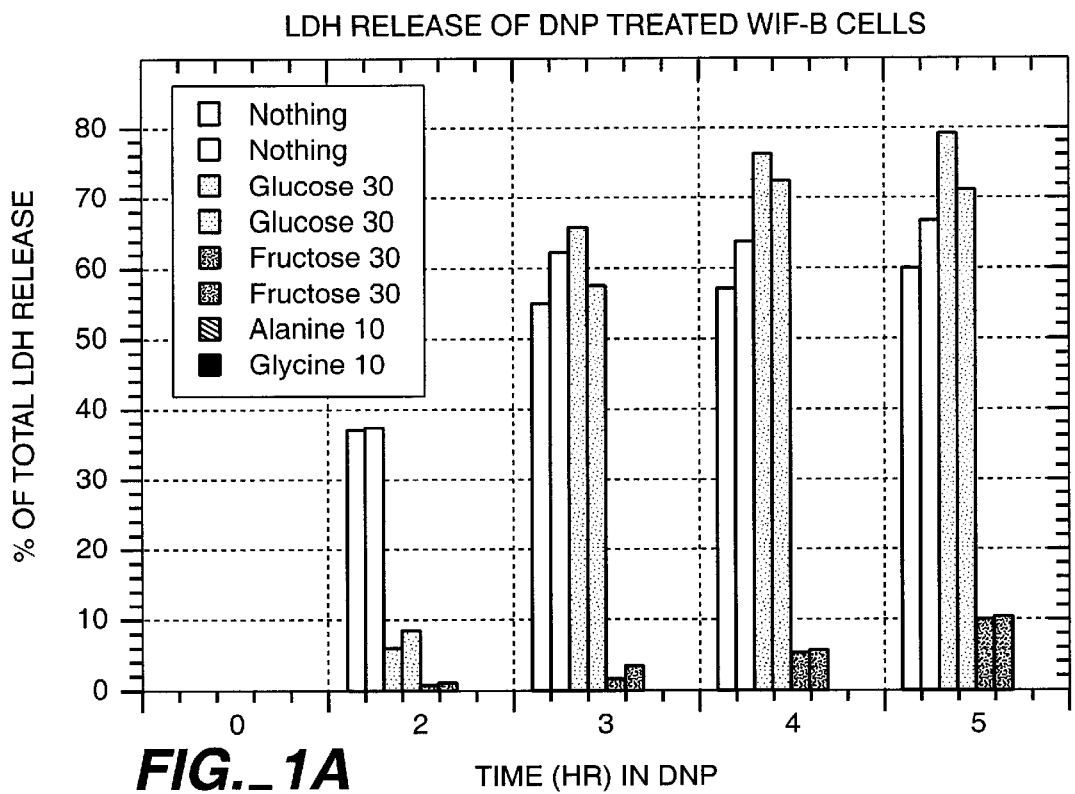
FIG._1A
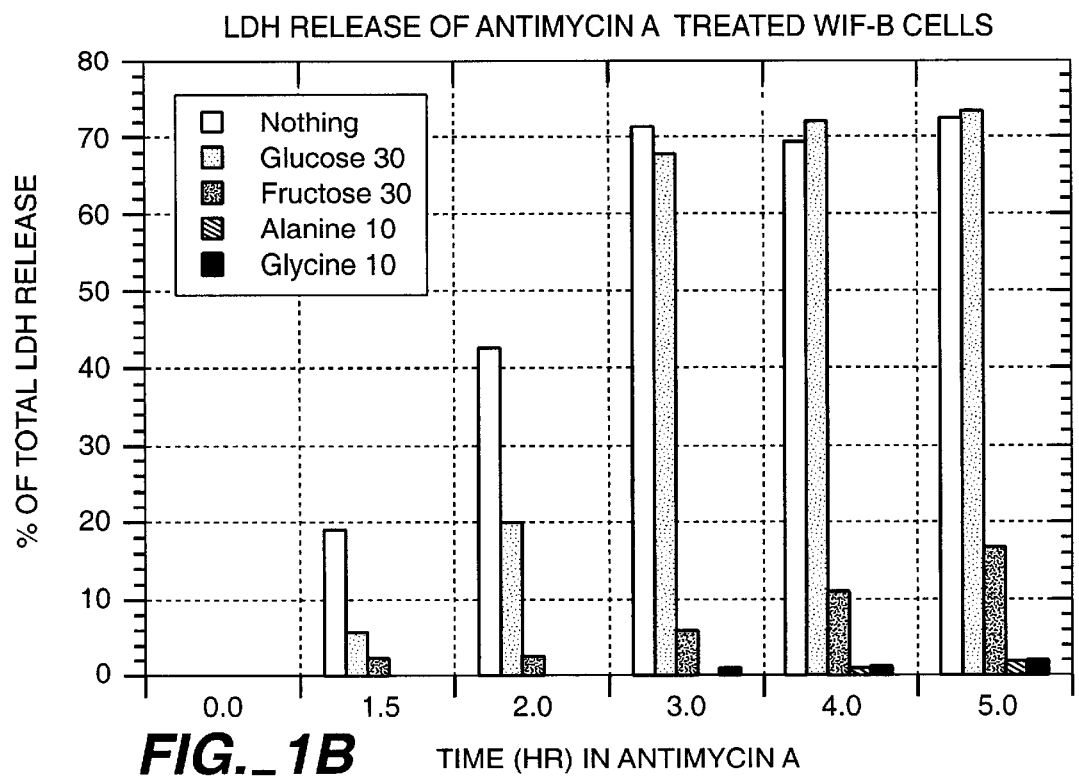
FIG._1B

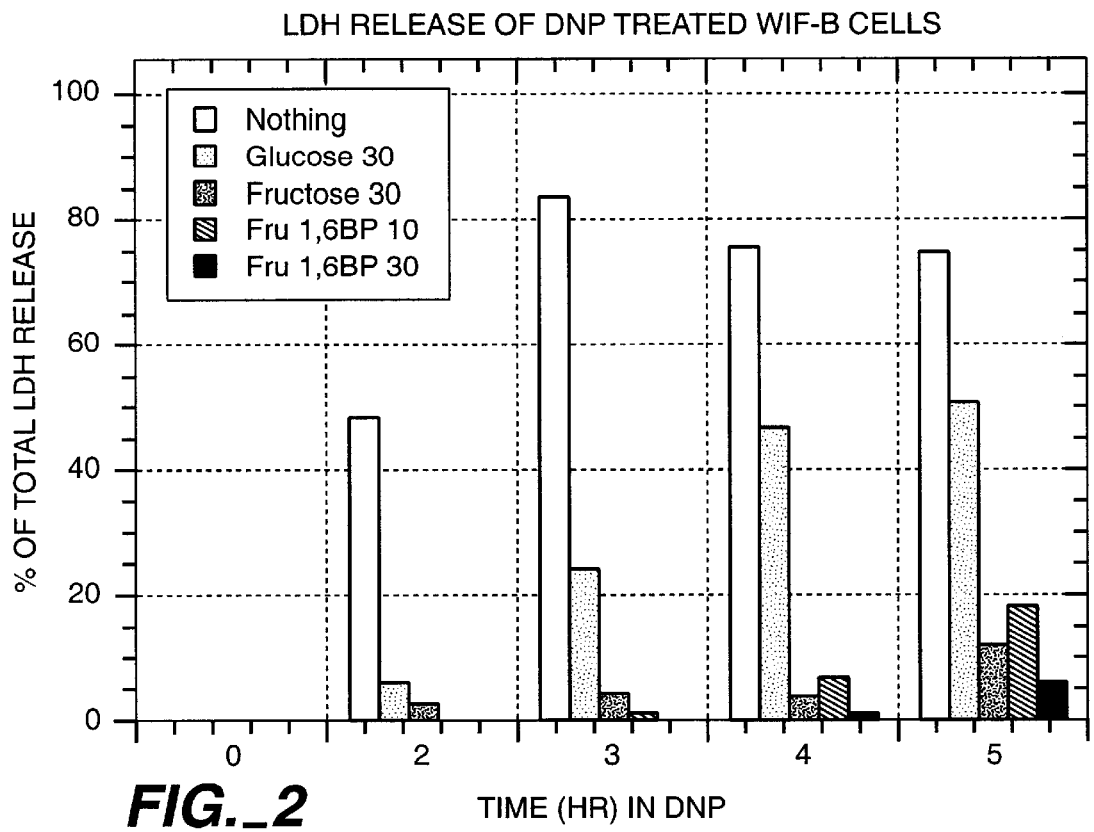
FIG._2
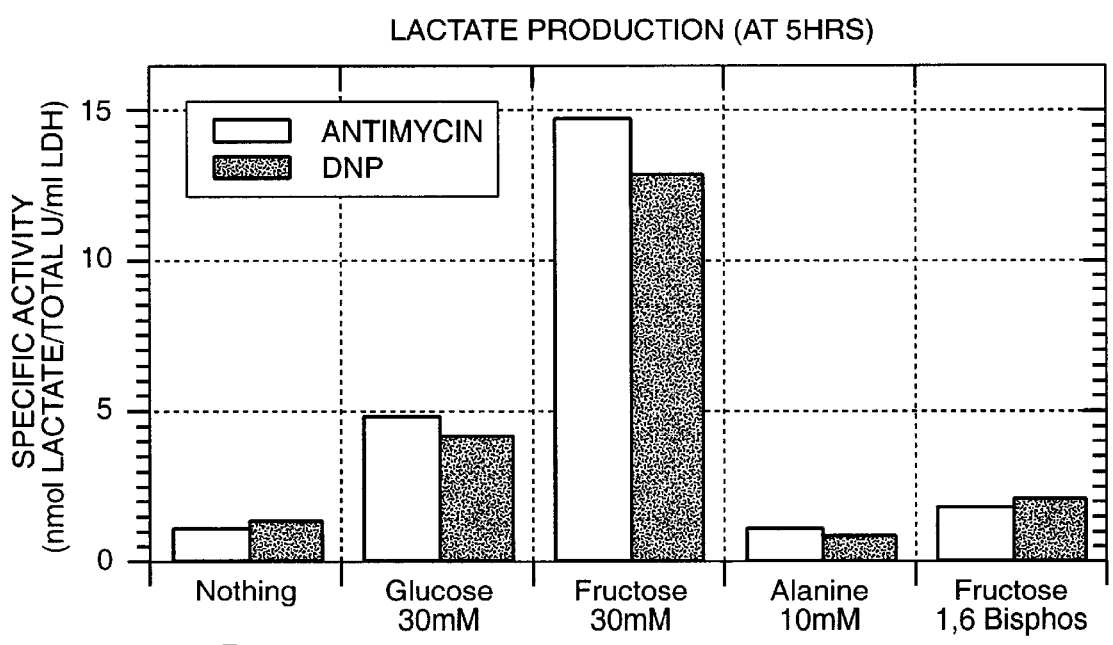
FIG._3

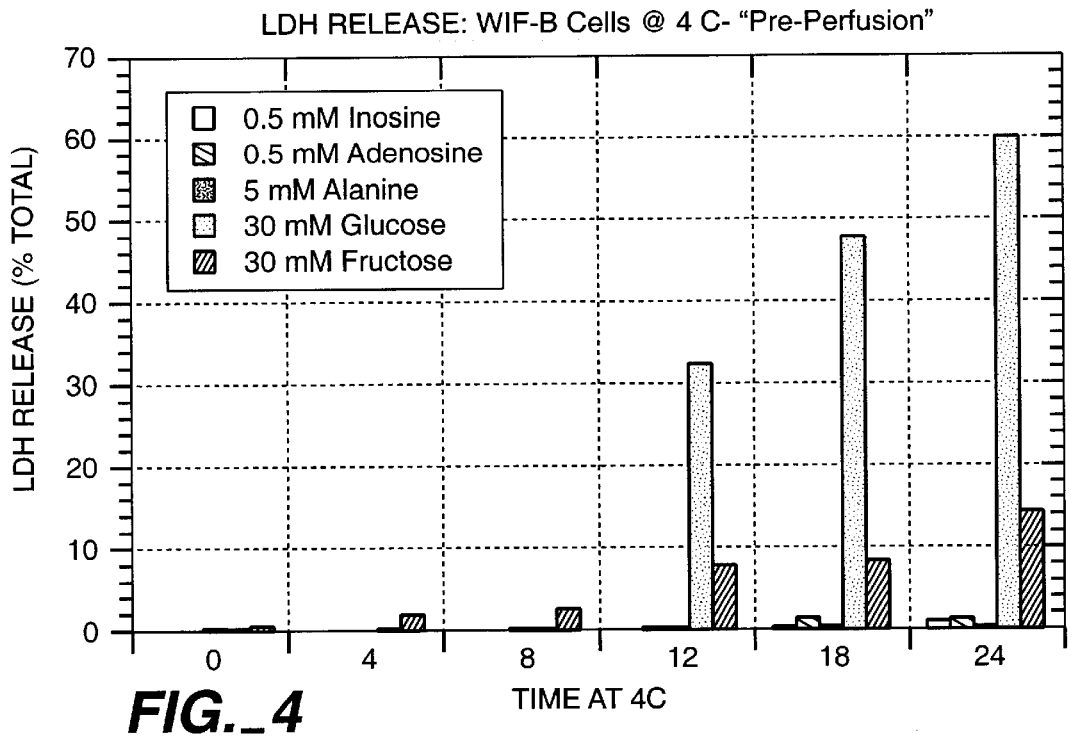
FIG._4
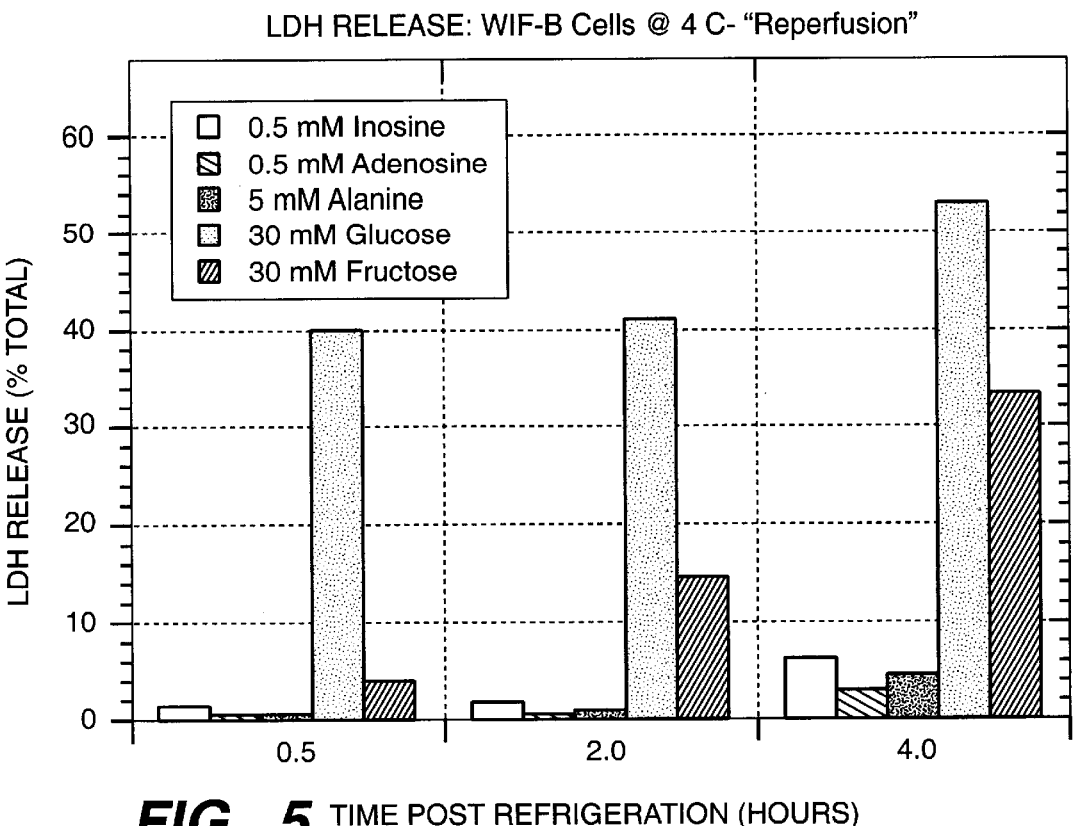
FIG._5

ASSAY SYSTEM FOR ANTI-STRESS AGENTS

BACKGROUND

Progress in the discovery and development of therapeutic agents for the treatment of hypoxic stress is limited by: 1) the absence of model systems in which to conduct studies into the cellular mechanism of injury; and 2) the inability to effectively screen putative lead compounds as potential therapeutic agents. Physiologic model systems are limited primarily by the poor mechanistic resolution, inconvenience, and limited ability to screen large numbers of compounds to develop lead molecules. Primary or transformed cell (culture) models are limited by alterations in cell energy metabolism secondary to transformation processes (reversion to alternative fuel substrates/pathways, such as glycolysis being substituted by oxidative phosphorylation). Also, there is a generalized lack of fidelity when compared to their primary derived tissue.

The preponderance of published data investigating the effects of hypoxia have been performed on whole animals, isolated organs, or primary cells. Tissues that succumb to the effects of hypoxia are characterized by high rates of oxidative metabolism and high cellular energy demand. Cells adapted to culture conditions are typically not ideal models for the study of the effects of hypoxia. They routinely possess fewer mitochondria and derive energy needs primarily by glycolysis, i.e., anaerobic metabolism. Hence, these cell types are resistant to the effects of hypoxia.

Previous studies employing primary renal cells rabbit proximal tubules), a highly oxidative tissue, demonstrated that both alanine and glycine effect considerable cytoprotection to the effects of tissue anoxia (Garza-Quintero et al. (1990) *Am. J. Phys.* 258; Renal *Elect. Phys.* 27:F1075–F1083). The cytoprotective effect of fructose 1,6-bisphosphate to the effects of hypoxia has also been described (Markov et al., (1980) *Am. Heart. J.* 100:639–646).

SUMMARY OF THE INVENTION

Methods and compositions are provided for screening cytoprotectant compositions for use in alleviating stress, such as hypoxia. A rat hepatoma cell line, WIF-B, is found to respond to mitochondrial inhibitors by releasing extracellularly lactate hydrogenase (LDH), as well as lactate, within a convenient period of time. Known cytoprotectants are found to reduce the rate of LDH release. The WIF-B cells are cultured in accordance with a convenient schedule, transferred to the assay medium and the mitochondrial inhibitor added. A cytoprotectant candidate may be added at any convenient time thereafter and the rate of LDH release into the medium is monitored. Reduction in LDH release is indicative of cytoprotection.

BRIEF DESCRIPTION OF THE DRAWINGS

FIGS. 1A and 1B are bar graphs of LDH release in response to dinitrophenol (DNP) and antimycin A, respectively;

FIG. 2 is a bar diagram of the effect of cytoprotective candidates on the rate of LDH release;

FIG. 3 is a bar diagram of lactate production induced by antimycin A or dinitrophenol in the presence and absence of cytoprotectant candidates;

FIG. 4 is a bar diagram of LDH release at 4° C. of WIF-B cells in the presence and absence of cytoprotectant candidates; and FIG. 5 is a bar diagram of LDH release of the refrigerated WIF-B cells at 37° C.

DESCRIPTION OF THE SPECIFIC EMBODIMENT

Assays are provided for screening large numbers of cytoprotectant candidates. The assay method employs a rat hepatoma-derived cell line described in lhrke et al., (1993) *J. Cell Biol.* 123:1761–1775; and Shanks et al., (1994) *J. Cell Science* 107:813–825. The cell line is referred to as WIF-B.

The cells are prepared for use in the assay by growing in an appropriate medium. Media which has been found satisfactory include Cassio modified HAM F-12 medium supplemented with sodium bicarbonate, antibiotics, hypoxanthine-aminopterin-thymidine, and 5% fetal bovine serum. The cells may be grown under normal conditions in a humidified incubator, conveniently 37° C. and about 7% carbon dioxide atmosphere, although a lesser percent carbon dioxide atmosphere may be used, e.g. 5%. The cells may be grown on any convenient container, such as any tissue culture treated plastic, glass surfaces e.g. coverslips, substrate coated surfaces (e.g. fibronectin, collagen, lysine, etc.), beads, holofibers, roller bottles, bioreactors, suspension cultures, and agarose entrapment. The medium is replaced in accordance with conventional schedules, conveniently initially, every other day for seven days, followed by changing the medium daily thereafter.

For subculturing, the cells may be dislodged from the flask by treatment with an appropriate protease. Conveniently trypsin may be used in conjunction with an appropriate proteolytic medium. After harvesting, the WIF-B cells may be seeded onto plastic or glass at a convenient density, usually in the range of about $0.5-5 \times 10^4$ cells/cm$^2$. For carrying the cell line, the cells may be grown to a density in the range of about $0.5-5 \times 10^5$/cm$^2$ over about one week. For experiments, cells are usually grown to higher densities, although these higher densities are not required, and are used at about 9–11 days post seeding.

After growth to the desired density, approximately one day following seeding onto glass coverslips, or other convenient support or container, WIF-B cells are individually placed into 6-well plates with 5 ml of culture medium. Prior to carrying out the assay, the culture medium is removed and the cells rinsed with 5 ml of a buffered balanced salt mixture, conveniently at or about physiological pH. After rinsing, the buffer is replaced with a small volume of the same buffered balanced salt mixture, with or without the cytoprotectant. Iso-osmolarity is maintained by the addition or removal of an appropriate amount of sodium chloride.

Following equilibration for 30 minutes at 37° C. under a normal atmosphere, a buffer aliquot is assayed for LDH activity (baseline LDH). A mitochondrial inhibitor is then added. Various mitochondrial inhibitors may be employed, such as antimycin A, dinitrophenol, rotenone, sodium or potassium cyanide, carbonyl cyanide m-chlorophenylhydrazone, carbonyl cyanide, p(trifluoromethoxy)phenylhydrazone, oxygen depletion. The concentration of the mitochondrial inhibitor will vary, being selected to allow for at least about 20%, usually at least about 50%, more usually at least about 60% LDH extracellular release into the media within the time of the assay, based on total LDH in the total assay composition (both intra- and extracellular), where the assay will usually occur within 3–8 hours, preferably about 4–6 hours. The medium may be assayed at convenient time intervals. After a predetermined time, or when at least about a desired percentage, conveniently at least about 20%, more usually at least about 60% of the LDH is released in the absence of a cytoprotectant, the medium is removed, the cells lysed, and the sample media and cell lysates assayed for LDH. Percentage LDH release is reported as the amount of extracellular LDH divided by the total LDH, extracellular LDH and in the lysate.

Similarly, lactate release may be monitored as exemplary of the response to hypoxia and its reversal with a cytoprotectant. In this instance, lactate may solely be followed in the medium, where the time for a predetermined amount of lactate generated in the presence of a mitochondrial inhibitor will be chosen to provide a convenient time for the assay and to provide for distinctions between different cytoprotectants. The assay may be carried out in the same manner as the assay for LDH, where lactate, by itself, or in conjunction with LDH release may be monitored. Cytoprotectant candidates may be added to the medium and their effect on the lactate release determined. The result may be compared with a known cytoprotectant added to a sample and the assay performed in the same manner. Lactate may be determined by the conversion of lactate to pyruvate by the enzyme lactate dehydrogenase.

The following examples are offered by way of illustration and not by way of limitation.

EXPERIMENTAL

Materials and Methods

Cells are maintained in Cassio modified HAM F-12 medium supplemented with sodium bicarbonate, antibiotics, hypoxanthine-aminopterin-thymidine, and 5% fetal bovine serum. Cells are maintained in Cassio modified HAM F-12 medium supplemented with 33 mM sodium bicarbonate, 50 μg/ml streptomycin, 200 Unit/ml penicillin G, 0.5 μg/ml amphotericin B, 10 mM sodium hypoxanthine, 40 μM aminopterin, and 1.6 mM thymidine (HAT), and 5% fetal bovine serum. The WIF-B cells are derived from a fusion of a HGPRTase$^-$rat hepatoma cell (FAO) and a normal human lung fibroblast (WI-38). The fibroblasts confer the ability of the fused cells to grow in the presence of HAT. The cells are kept at 37° C. in a humidified incubator with 7% $CO_2$ atmosphere. Cells are grown on plastic tissue culture flask or on glass coverslips. The medium was replaced every other day to day 7, then changed daily thereafter.

Subculturing was performed by dislodging cells from the flask by treatment with a solution containing 0.05% trypsin, 0.5 mM EDTA, 137 mM NaCl, 5.4 mM KCl, and 0.058% $NaHCO_3$. Following harvesting, WIF-B cells were seeded onto plastic flasks or glass coverslips at a density of $1-2\times10^4$ cells/cm$^2$. Cells used for carrying the cell line were grown to a density between $1-1.5\times10^5$/cm$^2$ in about 7 days. For assays, cells were grown to higher densities and used 9–11 days post seeding. The assay procedure was as follows: with these cells, 24 hours following seeding onto glass coverslips, WIF-B cells were individually placed into 6-well plates with 5 ml of culture medium. Prior to the assay, the culture medium is removed and the cells rinsed with 5 ml of a buffered balanced salt mixture containing: 1.3 mM $CaCl_2$, 1.2 mM $MgCl_2$, 5 mM KCl, 115 mM NaCl, 1 mM $K_3PO_4$ and 25 mM HEPES buffer, pH=7.4. After rinsing, the buffer was replaced with 5 ml of the same buffer, with or without the cytoprotectant candidate. Iso-osmolarity was maintained by the addition or subtraction of an appropriate amount of NaCl.

Following equilibration for 30 minutes at 37° C. at a normal atmosphere, 100–200 μl of buffer was assayed for LDH activity (baseline LDH). Antimycin A or dinitrophenol (DNP) was added and the medium sample at predetermined time intervals for a given candidate. After 5 hours, the medium was removed and the cells lysed with 1% Triton-X100 in 20 mM Tris buffer, pH=7.4. The sampled medium and cell lysates were assayed for LDH activity. LDH activity is defined as the percentage LDH in the extracellular medium as compared to the total LDH obtained by adding the LDH activity in the sampled medium and the cell lysate. LDH was measured using the Boehringer Mannheim Cytotoxicity kit (1 644 793).

An organ preservation assay was performed by seeding with WIF-B cells at a density of $2\times10^4$ cells/cm$^2$ onto 18 mm glass coverslips (day 1). On day 2, each coverslip was transferred to a well of a 6-well plate. Cells were subsequently allowed to propagate for an additional 8 days. On day 10, the medium was replaced with 25 mM HEPES buffered balanced salt solution, pH=7.4, containing one of the following test compounds: 30 mM glucose, 30 mM fructose, 0.5 mM adenosine, 0.5 mM inosine, or 5 mM alanine. The cells were then placed at 4° C. Aliquots were removed from the cell suspension buffer at predetermined time intervals and assayed for LDH activity. At 24 hours, the cell suspension buffer was replaced with HEPES bufferedbalanced salt solution, pH=7.4, containing 30 mM glucose. The cells were subsequently placed into a 37° C. incubator and alliquots of suspension buffer removed at 0.5, 2 and 4 hours and analyzed for LDH. The data was expressed as a percent of the LDH in the media divided by the total LDH (cells plus media) assayed in the media at the indicated time points.

Results

Exposure of WIF-B cells to antimycin or DNP results in a time dependent increase in the release of LDH (FIGS. 1A and 1B). After 5 hours, approximately 60–80% of the total LDH is released. The addition of a cytoprotectant either slows or nearly completely inhibits LDH release. Cells treated in the presence or absence of glucose demonstrated an about 70% release of the total LDH after 3 or more hours of exposure to antimycin or DNP. In contrast to glucose, fructose afforded significant protection to both antimycin and DNP mediated injury (approximately 10–20% vs. 70% at 5 hours). These observations are in agreement with published data demonstrating fructose protection of primary hepatocytes secondary to cyanide treatment or hypoxia (Anundi et al., (1987) *Am. J. Phys.* 253 (*Gastro Intest. Liver Physiol.* 16):G390–G396; DiMonte et al., (1988) *Biochem. Biophys. Res. Comm.* 153:734–740; Gores et al., (1988) *Am. J. Phys.* (*Cell Physiol.* 24):C315–C322; Wu et al., (1990) *Arch. Biochem. Biophys.* 282:358–362; and Snyder et al., (1993) *Am. J. Phys.* 264 (*Cell Physiol.* 33):C709–C714). As shown in FIGS. 1A and 1B, alanine and glycine provided considerable cytoprotection, where in the presence of 10 mM alanine or 10 mM glycine, minimal LDH release was observed (about 0–2%).

As shown in FIG. 2, fructose 1,6-bisphosphate afforded significant protection, where LDH release was about 10% relative to control.

Lactate production, which is associated with disruption in mitochondrial function, measured in parallel to LDH release was shown to increase in the presence of antimycin (FIG. 3). The WIF-B cells, with regards to lactate production during the inhibition of oxidated phosphorylation, behave in a manner similar to isolated organ and primary cell model systems.

FIGS. 4 and 5 show that in the organ preservation model, at 4° C., inosine, adenosine, alanine, and fructose provide substantial protection even up to 24 hours. When the cells are warmed to 37° C., inosine, adenosine, and alanine still afford substantial protection for an extended period of time, while the protection afforded by fructose is diminishing.

It is evident from the above results, that the subject assay provides for convenient, rapid methodology for screening cytoprotectant compounds for their protection against hypoxia. The WIF-B cells are found to be representative of oxidative tissue. The WIF-B cells are injured in a temporal sequence that resembles a similar time dependance as the isolated rat liver model and primary derived hepatocytes. Molecules which have been shown to be capable of conferring protection to hypoxia of primary hepatocytes, renal tubule cells and isolated rat livers, also confer protection from cell death in the WIF-B model system.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for assaying a candidate compound for cytoprotective property against mitochondrial inhibitors, said method comprising:

combining oxidative WIF-B hepatoma derived cells in a first assay medium comprising a mitochondrial inhibitor and combining oxidative WIF-B hepatoma derived cells in a second assay medium, wherein said second assay medium comprises said first assay medium, said mitochondrial inhibitor and a candidate compound;

incubating said WIF-B cells in said first assay medium and said WIF-B cells in said second assay medium; and comparing amount of lactate dehydrogenase (LDH) in the second assay medium with amount of LDH in the first assay medium, whereby a reduction in the amount of LDH in the second assay medium as compared to the amount of LDH in the first assay medium indicates the candidate compound has a cytoprotective property.

2. A method according to claim 1, wherein said mitochondrial inhibitor is antimycin A.

3. A method according to claim 1, wherein said mitochondrial inhibitor is dinitrophenol.

4. The method of claim 1, further comprising:

combining oxidative WIF-B hepatoma derived cells in a third assay medium, wherein said third assay medium comprises said first assay medium and a known cytoprotectant;

incubating said WIF-B cells in said third assay medium; and comparing the amount of LDH in the third assay media with the amount of LDH in the second assay medium, whereby a reduction in the amount of LDH in the second assay medium as compared to the amount of LDH in the first assay medium or the third assay medium indicates the candidate compound has a cytoprotective property.

5. A method according to claim 4, wherein said known cytoprotectant is adenosine, inosine, alanine, or glycine.

6. The method of claim 1, further comprising determining the amount of LDH in said first and second assay media at a plurality of time points.

7. A method for assaying a candidate compound for cytoprotective property during organ storage, said method comprising:

combining oxidative WIF-B hepatoma-derived cells in a first assay medium and combining oxidative WIF-B hepatoma derived cells in a second assay medium, wherein said second assay medium comprises said first assay medium and a candidate compound, and wherein said WIF-B cells are maintained for at least 12 hours at 4° C.;

determining amount of lactate dehydrogenase (LDH) in said first and second assay media;

transferring said WIF-B cells from said first assay medium to a third medium comprising first assay medium and glucose;

transferring said WIF-B cells from said second assay medium to a fourth medium comprising second assay medium and glucose;

incubating said WIF-B cells in the third and fourth media at 37° C.;

determining the amount of LDH in said third and fourth media at a plurality of time points; and comparing the amount of LDH in said third and fourth media, whereby a reduction in LDH in said fourth medium compared to said third medium indicates the candidate compound has a cytoprotective property during organ storage.

8. A method according to claim 7, wherein said WIF-B cells are maintained at 4° C. for 24 hours.

9. A method according to claim 7, wherein the reduction in amount of LDH in said fourth medium is compared with the reduction observed under the same conditions with a known cytoprotectant.

10. A method for assaying a candidate compound for cytoprotective property against mitochondrial inhibitors; said method comprising:

combining oxidative WIF-B hepatoma derived cells in a first assay medium comprising a mitochondrial inhibitor and combining oxidative WIF-B hepatoma derived cells in a second assay medium, wherein said second assay medium comprises said first assay medium, said mitochondrial inhibitor and a candidate compound;

determining amount of lactate present in the extracellular medium in each assay medium; and comparing the amount of lactate in the second assay medium with the amount of lactate in the first assay medium, whereby a reduction in the amount of lactate in the extracellular medium in the second assay medium as compared to the first assay medium indicates the candidate compound has a cytoprotective property.

* * * * *